US00PP19044P2

(12) United States Plant Patent
Olesen

(10) Patent No.: US PP19,044 P2
(45) Date of Patent: Jul. 22, 2008

(54) *MINATURE ROSE* PLANT NAMED 'POULPAL023'

(50) Latin Name: *Rosa hybrid*
Varietal Denomination: Poulpal028

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/711,237

(22) Filed: Feb. 26, 2007

(51) Int. Cl.
*A01H 5/00* (2006.01)

(52) U.S. Cl. ..... Plt./121
(58) Field of Classification Search ..... Plt./121
See application file for complete search history.

*Primary Examiner*—Kent L. Bell
*Assistant Examiner*—June Hwu

(57) ABSTRACT

A new miniature rose plant that has abundant, light pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa hybrid.*
Variety denomination: 'Poulpal028'.

SUMMARY OF THE INVENTION

The present invention constitutes a new and distinct variety of miniature rose plant which originated from a controlled crossing between the female seed parent, an unnamed seedling, and the male pollen parent 'Poulra014', U.S. Plant Pat. No. 14,941.

The two parents were crossed during the summer of 2001 and the resulting seeds were planted in a controlled environment in Fredensborg, Denmark. The new variety, named 'Poulpal028', originated as a single seedling from the stated cross.

The new variety may be distinguished from its female seed parent, primarily by flower color. The seed parent has deep pink flowers while 'Poulpal028' has light pink flowers.

The new variety may be distinguished from its male pollen parent by the following combination of characteristics:

1. The pollen parent has 30 to 35 petals under normal conditions with 5 to 7 petaloids, while 'Poulpal028' has 60 petals 15 to 20 of which are petaloids.
2. Flowers of the pollen parent have a general tonality of Red-Purple Group 62D, while flowers of 'Poulpal028' are typically Orange Group 27D with intonations of Red-Purple Group 62B.
3. The new variety has slightly larger flowers than those of the pollen parent.

The objective of the hybridization of this rose variety for commercial culture was to create a new and distinct variety with unique qualities, such as:

1. Uniform and abundant light pink flowers;
2. Vigorous and compact growth;
3. Year-round flowering under glasshouse conditions;
4. Suitability for production from softwood cuttings in pots;
5. Durable flowers and foliage which make a variety suitable for distribution in the floret industry.

This combination of qualities is not present in previously available commercial cultivars of this type, known to the inventor, and distinguish 'Poulpal028' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal028' was selected by the inventor as a single plant from the progeny of the hybridization in 2001.

Asexual reproduction of 'Poulpal028' by cuttings and traditional budding was first done by Mogens N. Olesen in the nursery in Fredensborg, Denmark in July of 2002. This initial and other subsequent propagations conducted in controlled environments have demonstrated that the characteristics of 'Poulpal028' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpal028'. Specifically illustrated in the drawing are flowers, flower buds, petals, leaves, and bare stem.

DETAILED DESCRIPTION OF THE VARIETY

The following is a description of 'Poulpal028', as observed in its growth in a field nursery in Fredensborg, Denmark. Observed plants are 12 months of age and were grown on Rosa multiflora understock. Color references are made using The Royal Horticultural Society (London, England) Colour Chart, 2001, except where common terms of color are used.

For a comparison, several physical characteristics of the rose variety 'Poulac018', U.S. Plant Pat. No. 15,150. are compared to 'Poulpal028' in Chart 1.

CHART 1

| | 'Poulpal028' | 'Poulac018' |
|---|---|---|
| Flower shape: | Double petaled, with a high pointed center which is tightly closed. | Deep cup. |
| Petalage: | 60 petals 15 to 20 of which are petaloids. | 90 petals under normal conditions with 10 petaloids. |
| General Tonality of Flower Color: | Orange Group 27D with intonations of Red-Purple Group 62B. | Red Group 49B to 49C with intonations of Red Group 36C. |

FLOWER AND FLOWER BUD

Blooming habit: Recurrent.

Flower bud:

*Size.*—Upon opening, 24 mm in length from base of receptacle to end of bud. 14 mm in diameter.

*Bud form.*—Broad based pointed ovate.

*Bud color.*—As sepals unfold, petals are Red Group 38 A with intonation of Red Group 36B.

*Sepals.*—Upper Surface: Color: Green Group 138B with weak intonations of Greyed-Orange Group 166A. Texture: Moderately Pubescent. Lower Surface: Color: Yellow Green Group 144A with weak anthocyanin the color of Greyed-Orange Group 166A. Texture: Smooth. Shape: Apex: Cirrhose. Base: Flat at union with receptacle. Margins: Margins medium foliaceous appendages on three of the five sepals. Size: Normally 30 mm long by 9 mm wide.

*Receptacle.*—Surface Texture: Smooth and glabrous. Shape: Urn-shaped. Size: 4 to 7 mm in height by 7 mm wide. Color: Yellow Green Group 144A.

*Pedicel.*—Surface: Smooth. Few stipitate glands observed. Length: 25 to 35 mm. Diameter: 2 to 4 mm. Color: Yellow-Green Group 144A. Strength: Strong.

*Peduncle.*—Surface: Smooth. Length: 20 to 30 mm average length. Diameter: 4 mm. Color: Yellow-Green Group 146B. Anthocyanic pigments Greyed-Orange Group 177A are of medium intensity.

*Borne.*—There are normally 3 to 5 flower buds per flowering stem, occurring in a corymb inflorescence type.

Flower bloom:

*Fragrance.*—Light floral.

*Duration.*—As a potted plant, flowers last from 21 to 28 days. As a field grown plant, flowers last up to 14 days. Petals do not fall cleanly away from the receptacle.

*Size.*—Average flower diameter is 65 to 75 mm when open. Flowers are normally 40 mm in depth.

*Form.*—General shape is double petaled, with a high pointed center which is tightly closed.

Shape of flower, side view: After opening, the upper portion of the flower is convex. The lower portion is concave.

*Petalage.*—There are normally 60 petals 15 to 20 of which are petaloids.

*Color.*—Upon opening, petals: Outermost petals: Upper Surface: Orange Group 27B overall with light intonations of Red Group 52C to 52D at the basal zone. Lower Surface: Red Group 49C with intonations of Red Group 55B at the basal to middle zone. Innermost petals: Upper Surface: Orange Group 27D to Yellow Group 11D overall with intonations of Red Group 52D at the basal zone. Lower Surface: Red Group 49C with intonations of Red-Purple Group 58D at the basal and middle zone. Upon opening, basal petal spots: Upper and lower surfaces have distinct colorations nearest Yellow Group 1D at the point of attachment. After opening, outermost and innermost petals: Upper Surface: Orange Group 27D overall with faint intonations the color of Red Group 38D. Lower Surface: Red Group 49C to Red-Purple Group 62D overall, with basal and middle zone intonations the color of Red Group 55B to 55C. After opening, basal petal spots: At the point of attachment, the upper and lower surfaces are Yellow-Green Group 150D. General Tonality: Orange Group 27D with intonations of Red-Purple Group 62B. There are no changes of tonality as flowers mature.

*Petals.*—Petal Reflex: Strong to very strong. Petal Margin: Entire and uniform. With none to weak undulations of margin. Shape: Generally broad elliptic. Base: Rounded. Apex: Rounded. Size: Outer petals are generally 38 mm long by 42 mm wide. Inner petals are generally 31 mm long by 28 mm wide. Thickness: Average. Texture: Smooth.

*Petaloids: Quantity: Normally, there are* 15 to 20. Size: 18 mm long; 12 mm wide. Shape: Apex is rounded. Base is acute. Generally the petaloids are shaped irregularly, with an occasional cleft in the margin. Color: Upper Surface: Orange Group 27D to Yellow Group 11D overall with intonations of Red Group 52D at the basal zone. Lower Surface: Red Group 49C with intonations of Red-Purple Group 58D at the basal and middle zone.

*Reproductive organs.*—Pollen: None observed. Anthers: Size: 1.5 mm long. Color: Yellow Group 13B. Quantity: 85 to 100. Filaments: Color: Yellow Group 7B and 4B. Length: Normally 3 mm. Pistils: Length: 6 mm long. Quantity: About 150. Stigmas: Equal in height relative to the length of the filaments and the height of the anthers. Color: Yellow Group 1D. Styles: Color: Yellow Group 1D with intonations of Red Group 48C. Seed formation: Not observed.

PLANT

*Plant growth.*—Upright. When grown on *Rosa multiflora* understock, the average height of the plant itself is 40 to 50 cm. The average width is 40 cm.

*Stems.*—Color: Young wood: Yellow-Green Group 144A. Older wood: Yellow Group 144A to 146B with intonations of Greyed-Purple Group 183B.

*Internodal distance.*—Length of stems: On average, canes are 35 cm from the base of the stem to the flowering portion. Diameter is 9 mm on average. Surface Texture: Young wood: Smooth. Older wood: Smooth.

*Prickles.*—None observed.

*Plant foliage.*—Normal number of leaflets on normal leaves in middle of the stem: 5. Compound Leaf size: Generally 180 mm (l)×120 mm (w). Quantity: 3 leaves per 10 cm of stem. Color: Leaf bearing angle to the stem: 45 degrees. Juvenile foliage: Upper Leaf Surface: Yellow-Green Group 146B. Lower Leaf Surface: Yellow-Green Group 147C. Anthocyanin, the color of Greyed-Red Group 178B observed at margins. Mature foliage: Upper Leaf Surface:

Yellow-Green Group 147A to 146A. Lower Leaf Surface: Yellow-Green Group 148B.

*Plant leaves and leaflets.*—Stipules: Size: 20 mm long. Shape: Linear, slightly broad based with outward extending apecies. Margins: Finely serrated with few stipitate glands. Color: Yellow-Green Group 146A to Yellow-Green Group 147A. Petiole: Length: Average 35 mm. Diameter is normally 2 mm. Color: Yellow-Green Group 144A on upper surface. Lower surface is Yellow-Green Group 144C. Upper Surface: Few stipitate glands. Lower Surface: Smooth. Rachis: Size: Normally 60 mm. Color: Yellow-Green Group 144A on upper surface. Lower surface is Yellow-Green Group 144C. Upper Surface: Few stipitate glands. Lower Surface: Smooth. Leaflet: Size: 70 mm in length by 50 mm wide. Margin: Serrate. General Shape: Elliptical. Apex Shape: Mucronate. Base Shape: Round. Texture: Smooth. Arrangement: Odd pinnate. Venation: Reticulate. Leaf Gloss: Matte finish.

Disease resistance: Above average resistance to powdery and downy mildew, black spot, and *Botrytis* under normal growing conditions in Fredensborg, Denmark.

What is claimed is:

1. A new and distinct variety of rose plant of the miniature class named 'Poulpal028', substantially as illustrated and described herein, due to its abundant, light pink flowers, vigorous growth, compact habit, suitability for production from softwood cuttings in pots, and durable flowers and foliage that make the variety suitable for distribution in the floral industry.

* * * * *

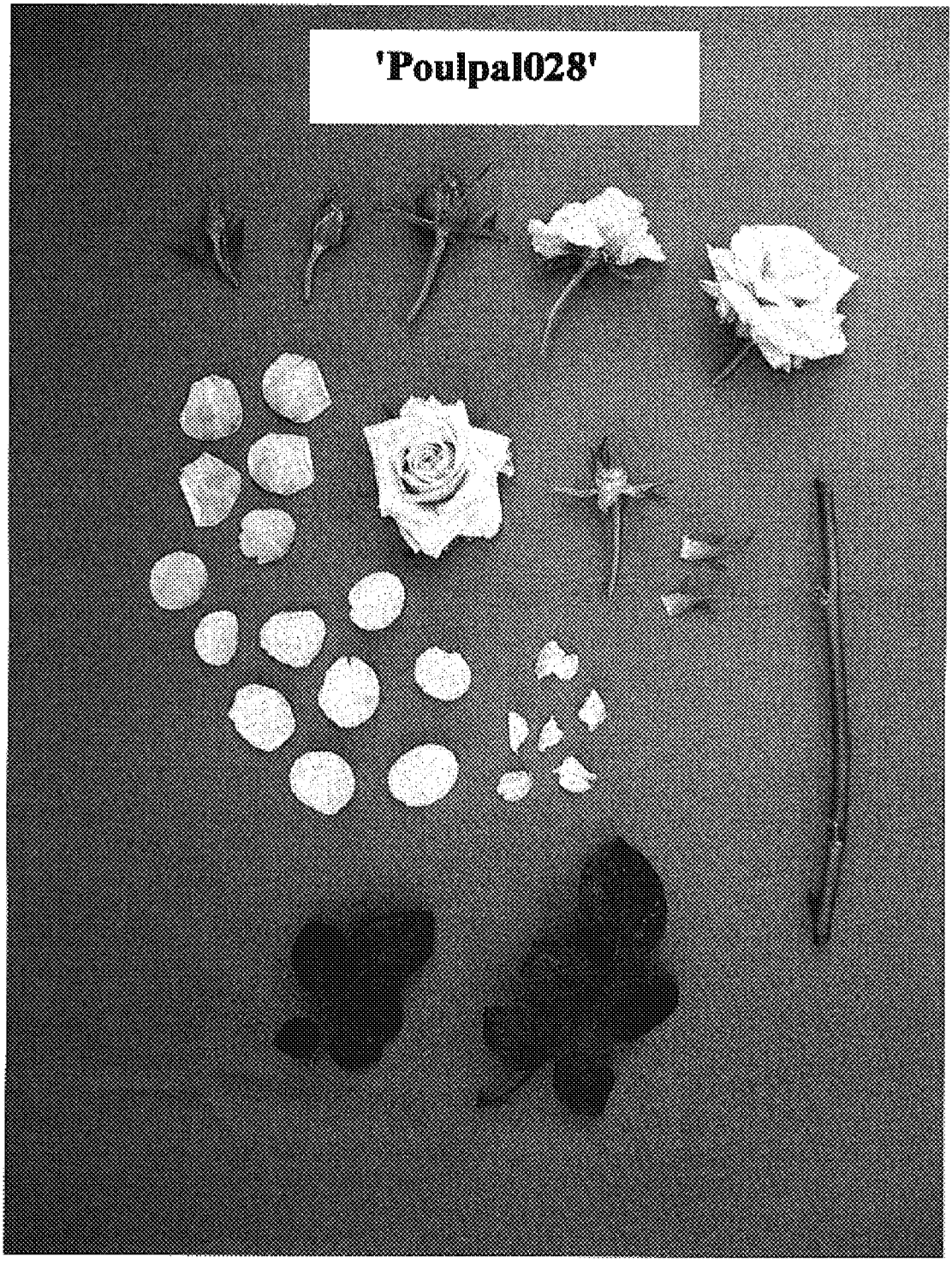
'Poulpal028'